United States Patent [19]
Zlokarnik et al.

[11] 4,162,971
[45] Jul. 31, 1979

[54] INJECTORS WITH DEFLECTORS FOR THEIR USE IN GASSING LIQUIDS

[75] Inventors: Marko Zlokarnik, Cologne; Klaus Elgeti, Bergisch Gladbach, both of Fed. Rep. of Germany

[73] Assignee: Bayer Aktiengesellschaft, Leverkusen, Fed. Rep. of Germany

[21] Appl. No.: 818,894

[22] Filed: Jul. 25, 1977

[30] Foreign Application Priority Data

Jul. 31, 1976 [DE] Fed. Rep. of Germany ....... 2634496

[51] Int. Cl.² ........................... C02B 3/08; C02C 1/12
[52] U.S. Cl. .................... 210/15; 210/63 R; 210/220; 261/123; 261/DIG. 75
[58] Field of Search ..................... 137/604; 210/14, 15, 210/60, 63 R, 194, 197, 220, 221 R; 239/428.5, 433, 434.5; 261/77, 78 A, 123, DIG. 75; 366/167, 172, 173; 417/174

[56] References Cited

U.S. PATENT DOCUMENTS

| | | | |
|---|---|---|---|
| 399,200 | 3/1889 | Koehler | 261/77 |
| 466,310 | 12/1891 | Ritter | 261/77 X |
| 2,097,605 | 11/1937 | Schierenbeck | 261/78 A X |
| 2,479,403 | 8/1949 | Powers | 210/14 X |
| 3,206,032 | 9/1965 | Nottingham et al. | 261/77 X |
| 3,271,304 | 9/1966 | Valdespino et al. | 261/77 X |
| 3,336,016 | 8/1967 | Schreiber | 261/123 |
| 3,846,292 | 11/1974 | Lecompte, Jr. | 210/220 X |
| 3,938,738 | 2/1976 | Nagel et al. | 239/428.5 X |
| 4,044,079 | 8/1977 | Tveit | 261/DIG. 75 |

FOREIGN PATENT DOCUMENTS

| | | | |
|---|---|---|---|
| 2401466 | 7/1975 | Fed. Rep. of Germany | 210/220 |
| 1116081 | 5/1956 | France | 261/78 A |

*Primary Examiner*—Robert H. Spitzer
*Attorney, Agent, or Firm*—Sprung, Felfe, Horn, Lynch & Kramer

[57] ABSTRACT

In an injector for the dispersion of a gas into a liquid and comprising a gas inlet, a liquid inlet, and a mixing chamber communicating with said inlets and having an inlet and an outlet, the improvement which comprises at least one deflecting element disposed in the mixing chamber along the axis of the liquid inlet, whereby the liquid is distributed across the full cross-section of the mixing chamber. The deflector may be flat, conical or parabolic or it may be axially offset relative to the mixing chamber as a tongue. Special configurations are shown which are especially suited for use in treating liquid effluents and in fermentation processes.

15 Claims, 15 Drawing Figures

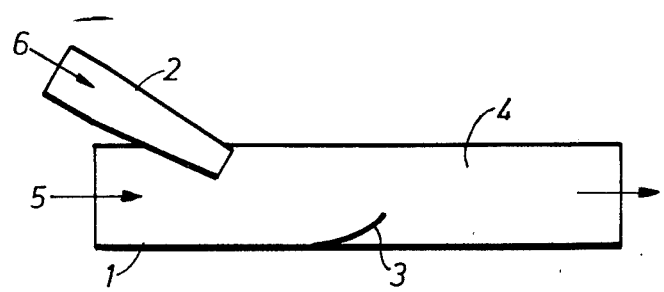
FIG. 1
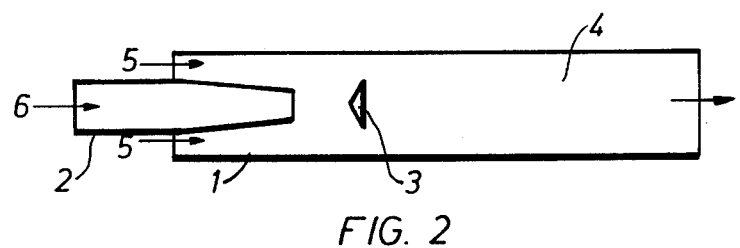
FIG. 2
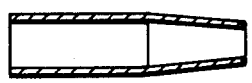   
FIG. 3          FIG. 4
      
FIG. 5     FIG. 6     FIG. 7

INJECTORS WITH DEFLECTORS FOR THEIR USE IN GASSING LIQUIDS

In order to intensify mass transfer in a gas-liquid system, amongst other things, two-component nozzles such as injectors, ejectors discharge nozzles and venturi nozzles, etc., are employed. In all of these devices the kinetic energy of the liquid jet (hereafter called the propulsion jet) is used for the dispersion of gas throughput into gas bubbles which are as fine as possible. Such devices are being increasingly used as gas distributors in bubble columns and particularly for supplying biological waste water treatment plants with gases containing oxygen (see German Offenlegungsschriften Nos. 2,400,416, 2,404,289, 2,408,064, 2,410,574, 2,516,371, and 2,458,449).

When changing from two component nozzles having a small diameter (diameter of the propulsion jet nozzle $\leq 10$ mm) to a larger diameter (diameter of the propulsion jet nozzle $\geq 10$ mm), the disadvantage of considerably lower efficiency with regard to the gas-liquid interface produced, must be taken into account and this is noticeable, for example, in the lower specific oxygen uptake [ kg $O_2$/kWh ] obtained.

This state of affairs is related to the fact that the circumferential part of the propulsion jet is more involved in the dispersion of the gas than its core. As the propulsion jet diameter increases, the cross-section of the jet increases in proportion to the square thereof, while its circumference increases only linearly, and this causes an increasingly smaller proportion of the kinetic energy of the propulsion jet throughput to be used for the dispersion of the gas in two-component nozzles (cf. M. L. Jackson AiChE J. 10 (1964) 6, 846/842; M. L. Jackson and W. D. Collin, I & EC Process Design and Develop. 3 (1964) 4, 386/393).

The object of the present invention is to design new injectors which maintain their efficiency with regard to the gas-liquid interface produced, even when the diameter of the propulsion jet nozzle increases.

The present invention, therefore, relates to injectors which are particularly suitable for the intensification of mass transfer in a gas-liquid systems because the kinetic energy of their propulsion jet is utilized with a high efficiency for producing very fine gas bubbles. They are characterized by the fact that at least one deflecting element is arranged on the propulsion jet axis in the mixing chamber.

The present invention also relates to a process for the intensification of mass transfer in gas-liquid systems by contacting a gaseous medium with a liquid medium, so that the energy of the propulsion jet is utilized for the production of very fine gas bubbles.

This is characterized by deflecting a liquid jet having a velocity of about 5 to 30 meters per second after leaving the nozzle and intimately contacting it with the gas within at least one subsequent mixing chamber where the ratio of gas throughput in standard $m^3$ per hour to the propulsion jet throughput in $m^3$ per hour is regulated to about 1 to 20, preferably to about 2 to 5.

In order to thoroughly mix the gas with the propulsion jet liquid, different designs of the apparatus and of the process will be proposed by the present invention. According to the design, one or more deflecting elements are arranged on the axis of the propulsion jet. The propulsion jet impinges upon the deflecting element, which is designed and positioned in such a way that it sprays the propulsion jet liquid over the entire cross-section of the mixing chamber. Deflecting elements which may be used in the present invention for the case of injectors having propulsion jet nozzle diameters $\geq 10$ mm include, for example, tongues arranged eccentrically in the mixing chamber, concentrically positioned cylindrical or conical bodies and retational bodies having a parabolically concave profile, which deflects or distribute the propulsion jet.

Further details of the size and geometrical arrangement of the injectors according to the invention are given in conjuction with the designs described below.

According to the invention, the gas which is to be mixed with the propulsion jet may be fed in any direction into the mixing chamber with regard to the propulsion jet.

The invention will be further described with reference to the accompanying drawings wherein:

FIGS. 1 and 2 are schematic sectional elevation of two different designs of injectors in accordance with the present invention;

FIGS. 3 and 4 are sectional elevation of two different propulsion jet nozzles for use in the injectors;

FIGS. 5, 6 and 7 are side elevations of three different deflectors which are to be positioned on the axis of the propulsion jets.

Figures 8, 9:
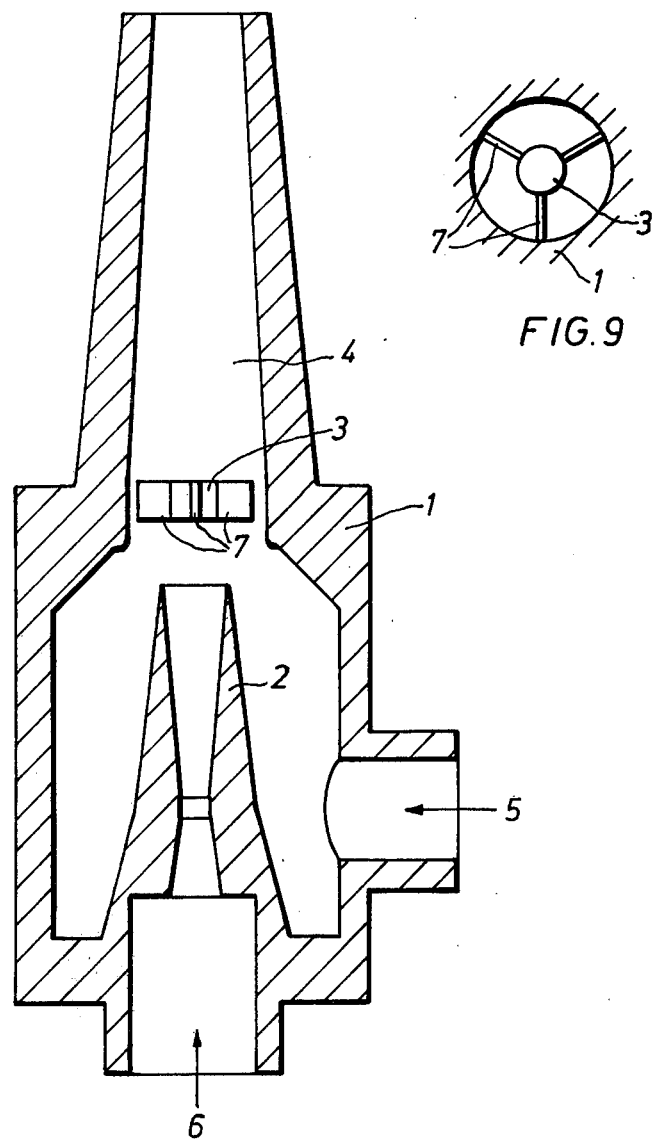
FIG. 8 is a sectional elevation of a preferred injector in accordance with the present invention.
FIG. 9 is a sectional plan of the deflecting element of FIG. 8.

The numerals in the figures have the following meanings:
1. Pipe or housing
2. Propulsion jet nozzle
3. Deflecting element
4. Mixing chamber
5. Gas inlet
6. Propulsion jet inlet
7. Deflecting element mounting
8. Cut out segments in the mixing chamber.

In more detail, FIG. 1 shows a pipe 1 made, for example, of metal such as for example brass or stainless steel, but preferably of plastic, such as for example polypropylene. The propulsion jet nozzle 2 protrudes into the pipe in such a way that its axis is at an acute angle with the axis of the pipe. At the point where the propulsion jet meets the opposite wall of the pipe, a deflecting element 3 in the form of a curved tongue or in the form of a weir is so positioned that the propulsion jet is deflected and distributed as uniformly as possible over the entire cross-section of the pipe. Section 4 of the pipe which is downstream of the deflecting element 3 is the mixing chamber in the sense of the present invention, where the gas introduced via a gas inlet 5 is thoroughly mixed with the propulsion jet introduced via a propulsion jet inlet 6. Here the gas continuum is dispersed into very fine gas bubbles which subsequently leave the mixing chamber together with the liquid and, after the jet has lost its kinetic energy to the surrounding liquid it becomes a bubble swarm which rises slowly up the liquid thus producing an intensive mass transfer between the gas and the liquid. In another design (not shown in the drawings), the propulsion jet may be deflected by bending the pipe at the position of the tongue shown in FIG. 1, in a way which makes the tongue or weir superfluous.

In the design shown in FIG. 1 of the present invention, the propulsion jet is deflected eccentrically in the pipe 1. However, the deflecting should preferably be so effected that the propulsion jet is only at most slightly twisted in order to utilize the kinetic energy of the propulsion jet for high efficient dispersion.

In the design shown in FIG. 2, the propulsion jet nozzle 2 is arranged concentrically in the pipe 1. Here the deflecting element 3 which distributes the propulsion jet should be mounted on the axis of the pipe, whereby the propulsion jet is uniformly distributed over the cross-section of the pipe and symmetrically with respect to the axis. In this design particularly favorable results are obtained with respect to the efficiency of gas-liquid contacting, if a cylinder having a flat base as shown in FIG. 5 is used as deflecting element. In the case of injectors with larger propulsion jet nozzle diameters (preferably greater than 20 mm), deflecting elements in the form of flat cones (FIG. 6) or rotational bodies having a parabolically concave profile (FIG. 7) are, in some cases, preferable to plane deflectors.

The distribution of the propulsion jet when it impinges upon the deflecting element may be aided by a corresponding configuration of the propulsion jet nozzle. A slightly conically tapered propulsion jet nozzle (FIG. 3) produces a so-called smooth jet which is distributed mainly by the deflecting element. On the contrary propulsion jet nozzles having a conically diverging opening (FIG. 4) produce slightly spread out propulsion jets with rough surfaces, which require less kinetic energy to be distributed uniformly over the cross-section of the mixing chamber 4 than in the case of the smooth jet. Furthermore, a circular deflecting element may in this case, be about 20 to 50% smaller in diameter.

FIG. 8 shows a preferred design of the present invention. This comprises a housing 1 preferably made from plastic and which is concentrically symmetrical around the propulsion jet axis apart from the gas inlet 5. The propulsion jet liquid is supplied via the inlet 6 to the propulsion jet nozzle 2. The deflecting element 3 is positioned centrally on the propulsion jet axis and is fixed by means of three mountings 7 which are spaced from one another by 120°. This is shown in the sectional plan (FIG. 9). The mixing chamber 4 tapers initially in the direction of flow of the gas/liquid mixture.

As a result of the distribution of the liquid jet using a deflecting element, the efficiency of the gas-liquid contacting as well as the adaptability to the properties of the liquid for example viscosity can now be further optimized by additional parameters such as the shape and size of the deflecting element, the shape of the propulsion jet nozzle, and the distance between the propulsion jet nozzle and deflecting element.

In the design shown in FIG. 1, the propulsion jet nozzle 2 is preferably inclined to the pipe axis at an acute angle of less than about 45°. When the throat diameter of the propulsion jet nozzle (denoted below as d is introduced as characteristic length the deflecting element 3 should be situated at a distance of about 1 to 3 d from the outlet end of the propulsion jet nozzle. The pipe 1 should have a diameter of about 2 to 5 d, preferably about 2 to 3 d, while the mixing chamber 4, i.e. the section of pipe which begins at the deflecting element 3, should be about 8 to 20 d long.

Correspondingly, the distance between the end of the propulsion jet nozzle outlet and the deflecting element 3 in FIG. 2 should also be about 1 to 3 d and the pipe diameter should be of about 2 to 3 d. The mixing chamber beginning downstream of the deflecting element 3 should be about 5 to 20 d long.

The following dimensions are recommended for the design shown in FIG. 8. The propulsion jet nozzle should be about 5 to 10 d, preferably about 6 to 8 d long. It initially tapers conically (with an angle of about 5 to 25°), and then widens with an angle of about 2 to 7°. The deflecting element 3 is positioned at a distance of about 1 to 3 d from the outlet of the nozzle 2. The deflecting element itself preferably has a diameter of about 0.5 to d, and the pipe surrounding the deflecting element at this point a diameter of about 3 d. The mixing chamber downstream of the deflection element comprises an initial pipe section which tapers conically and is about 5 to 20 d, preferably about 10 to 15 d long. The end of this pipe section has a diameter of about 1 to 3 d and an angle of taper of about 2 to 7°. Downstream of this pipe section the mixing chamber comprises a diffuser which is about 3 to 8 d preferably about 4 to 6 d long and whose angle of widening is about 5° to 20°.

The injectors according to the invention operate with the greatest efficiency in gas-liquid contacting under the following conditions:

The propulsion jet velocity in the throat of the propulsion jet nozzle should be between 5 and 30, preferably between 10 and 20 m per second. The ratio of the gas throughput in $m_N^3$ (standard cubic meters per hour) to the propulsion jet throughput in $m^3$ per hour is regulated to values of about 5 to 20, preferably about 3 to 6.

If the injectors according to the invention are used in their recommended application as gas distributors in biological waste water treatment plants where biologically degradable substances are treated by microorganisms which require oxygen then they are preferably inclined towards the base. This arrangement ensures that the gas-liquid jet leaving the injector enhances the circulation at the base thus preventing solids from settling. This arrangement has another advantage.

The gas-liquid jet which leaves the injector only loses its kinetic energy and disintegrates to a gas bubble swarm at a distance of about 50 to 80 d from the injector outlet. It is, therefore, advisable to arrange injectors in such a way that the gas bubble swarm is formed directly above the base of the basin, so that the gas bubbles can rise through the full liquid height.

Figure 10:
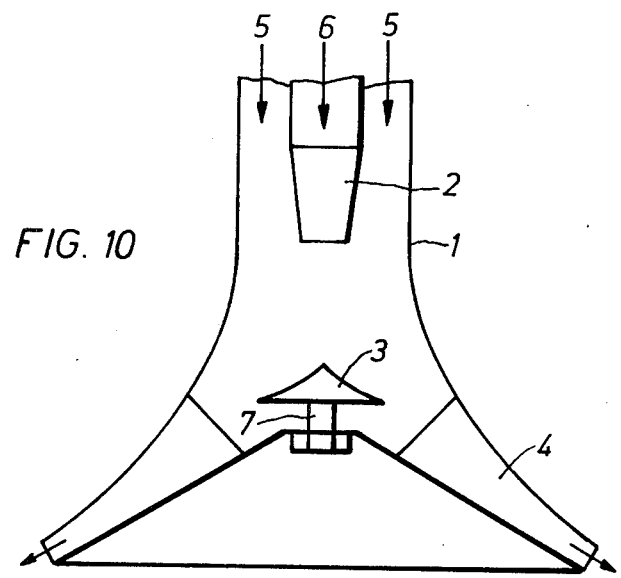
FIG. 10 is a schematic sectional elevation of an injector having multiple mixing chambers.
Figure 11:
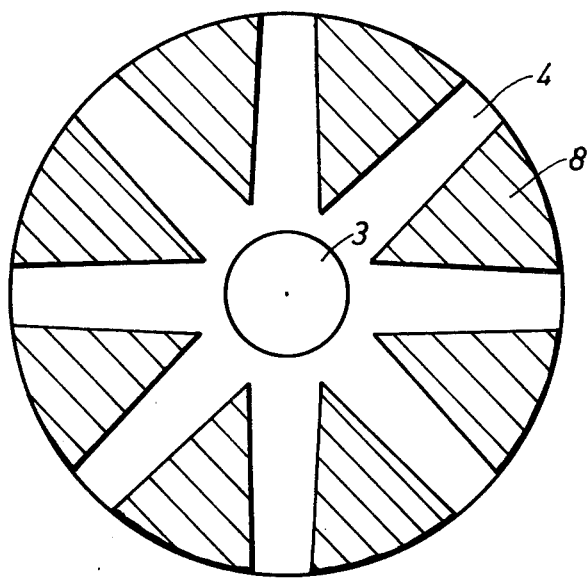
FIG. 11 is a sectional plan of the funnel shaped mixing chamber of the injector of FIG. 10.
Figure 12:
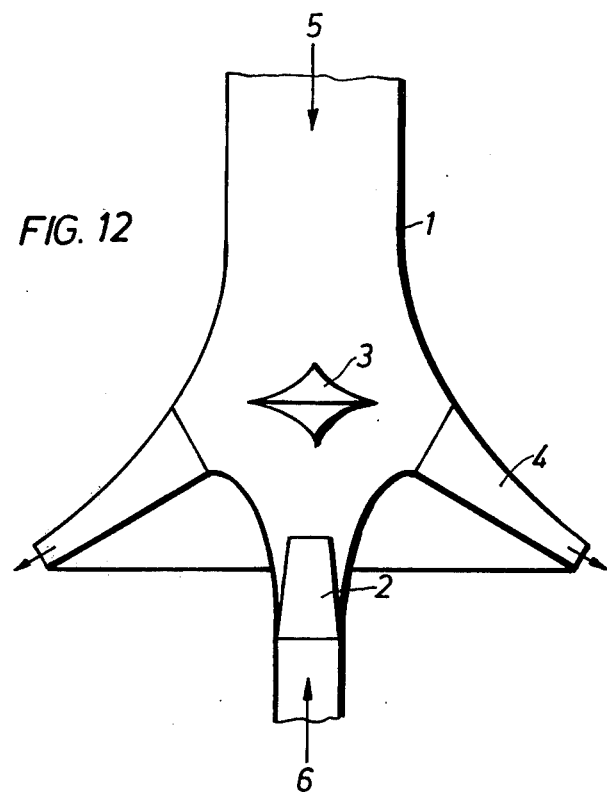
FIG. 12 is a schematic sectional elevation of another injector having multiple mixing chambers.

The injectors, according to the invention, may be combined in clusters of four or more in order to uniformly distribute the gas over the whole base of the basin. In this arrangement, the propulsion jet nozzles may be supplied with liquid and the gas inlets supplied with gas via a liquid and a gas manifold respectively. Whereas in this arrangement, the individual injectors maintain their particular shape, as shown for example in FIGS. 1, 2 and 8, the individual injectors of the cluster can alternatively be combined to form a single injector, which may be referred to as a funnel injector. FIGS. 10, 11 and 12 show exemplary design of such funnel injectors. FIG. 10 is a longitudinal cross-section of a funnel injector and FIG. 11 a sectional plan thereof. The propulsion jet leaves the propulsion jet nozzle 2 and impinges against the deflecting element 3, so that the propulsion jet is distributed over the entire cross-section of the mixing chamber 4 which is funnel shaped. The mixing chamber 4 is so designed that its cross sectional area decreases towards the outlet and the dispersion of the gas and liquid is thus accelerated. The slot at the outlet of the mixing chamber should have height of about 20 to 30 mm. In order to maintain this height, it is advisable in larger devices to remove segments of the funnel-shaped mixing chamber.

In the design in FIG. 12, gas and liquid are supplied from opposite directions to the deflecting element 3 and are deflected into the individual mixing chambers 4.

The injectors described above are capable of mixing a gas with a liquid efficiently even in the case of relatively large propulsion jet diameters and may easily be adapted to a given system (i. e. a given gas which is to be mixed with a given liquid). The gas dispersion leaving the mixing chamber of the injectors, according to the invention, is very rapidly mixed into the surrounding liquid so that the coalescence of the small gas bubbles to larger bubbles is substantially checked. The oxygen uptake in an effluent containing activated sludge is up to 50 % higher compared with conventional two-component nozzles for the same power-input.

If liquids with a marked tendency for gas bubble coalescence are contacted with gas, it is often not worth using much propulsion jet energy in producing very fine gas bubbles since these coalesce very rapidly into larger bubbles. In this case, the funnel injectors offer an energetically advantageous way of producing primary gas bubbles of stable size and small size distribution by merely shortening the mixing chamber. An injector whose mixing chamber has been reduced to an annular slot produces primary gas bubbles having a size which otherwise would have been produced upon completion of coalescence in the bubble swarm. In contrast to the production of very fine primary gas bubbles, the propulsion jet would require, in this case only about half the power.

Figure 13:
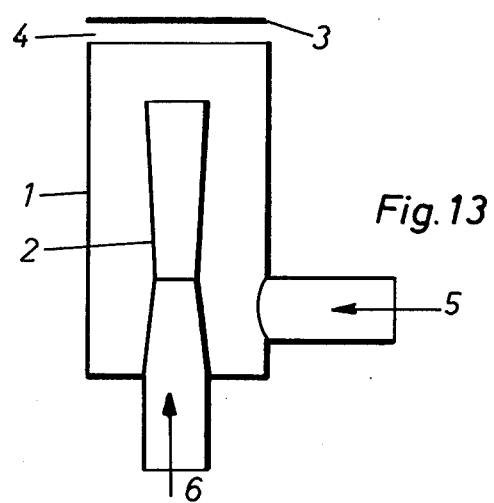
FIGS. 13 to 15 are schematic sectional elevations of different designs of injectors in accordance with the invention.
Figure 14:
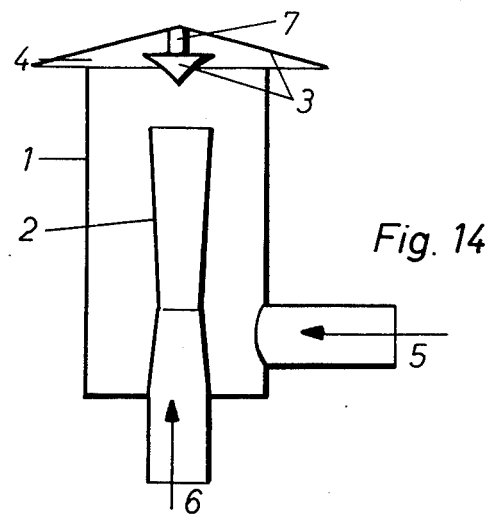
Figure 15:
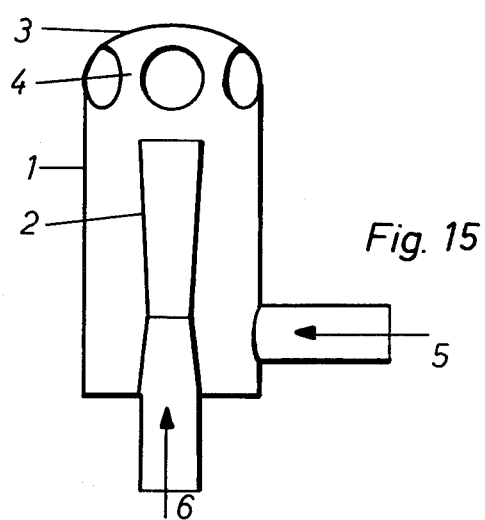

FIGS. 13 to 15 show by way of example three designs of this type of injector. In these designs a planar (FIG. 13) or roof-shaped (FIG. 14) or concave (FIG. 15) end surface serves as the deflecting element 3 for the propulsion jet, and in the design in FIG. 14, an additional deflecting element 3 may be used. The designs of FIGS. 13 and 14 have an outlet slot over the entire circumference of the pipe, and in the design in FIG. 15, circular openings (to be understood as constituting an interrupted annular slot in the sense of the present invention) are removed from the circumference of the pipe 1 instead of an annular slot. These openings should be designed with regard to the properties of the liquids used.

In these designs, the following dimensions are recommended: The distance between the propulsion jet nozzle and the deflecting element is about 1 to 3 d (d = throat of the propulsion jet nozzle); the pipe diameter is about 3 to 5 d, the width of the slot is about 0.5 to 1.5 d, preferably about 1 d. The ratio of standard gas to liquid throughput amounts in this case to about 5 to 15 and the propulsion jet velocity is about 5 to 20 m per sec.

Injectors of this class are very efficient gas distributor even in the case of relatively large propulsion jet diameters, and they may easily be suited to a specific system. The oxygen uptake in an effluent containing activated sludge is also in this case up to 50 % higher at the same power-input as compared to conventional injector nozzles.

It will be appreciated that the instant specification and claims are set forth by way of illustration and not limitation, and that various modifications and changes may be made without departing from the spirit and scope of the present invention.

What is claimed is:

1. In an injector for the dispersion of a gas into a liquid and comprising a gas inlet, a liquid inlet, and a mixing chamber communicating with said inlets and itself having an inlet and at least one outlet, the improvement which comprises positioning said liquid inlet axially of the mixing chamber, positioning said gas inlet upstream of the mixing chamber so as to provide a gas stream surrounding the liquid stream with both streams aimed in the same direction, and providing one deflecting element disposed in the mixing chamber along the axis of the liquid inlet, whereby the liquid is distributed across the full cross-section of the mixing chamber.

2. An injector according to claim 1, wherein the deflecting element is flat facing the liquid inlet.

3. An injector according to claim 1, wherein the deflecting element is conical facing the liquid inlet.

4. An injector according to claim 1, wherein the deflecting element has a parabolically concave longitudinal section facing the liquid inlet.

5. An injector according to claim 1, wherein the liquid inlet is a tube which first converges conically and then diverges conically at its end.

6. An injector according to claim 1, wherein the deflecting element is spaced from the liquid inlet at a distance of about 1 to 3 times the throat diameter of said inlet.

7. An injector according to claim 1, wherein the mixing chamber includes an upstream section which converges conically and a downstream section which diverges conically.

8. An injector according to claim 1, wherein the length of the mixing chamber is about 8 to 20 times the throat diameter of the liquid inlet.

9. An injector according to claim 1, wherein at least two mixing chambers are provided for each liquid or gas inlet.

10. An injector according to claim 1, wherein the mixing chamber is in the form of an annular passage.

11. An injector according to claim 10, wherein said annular passage comprises a plurality of laterally spaced mixing chambers.

12. In a process for intensifying mass transfer in a gas-liquid system by causing a gaseous medium to make contact with a liquid medium utilizing the energy of a propulsion jet for producing very fine gas bubbles, the improvement which comprises impinging the liquid medium at a velocity of between about 5 to 30 meters per second against a deflecting surface so as to bring the liquid into intimate contact with gas in at least one subsequent mixing chamber which tapers continuously, the gas throughput in $m_N^3$ per hour being about 2 to 20 times the throughput of the propulsion jet in $m^3$ per hour, the liquid and gas being introduced through an injector which houses the mixing chamber, the injector being provided with a liquid inlet axially of the mixing chamber, a gas inlet positioned upstream of the mixing chamber so as to provide a gas stream surrounding the liquid stream with both streams aimed in the same direction, and a deflecting element disposed axially in the mixing chamber and against which the liquid jet impinges.

13. A process according to claim 12, wherein the gas-liquid system is aerated sludge.

14. The process according to claim 13, wherein the gas throughput in about 2 to 5 times the propulsion jet throughput.

15. A process according to claim 12, wherein the gas-liquid system is an aerobic fermentation.

* * * * *